US008889379B2

(12) United States Patent
Tran et al.

(10) Patent No.: US 8,889,379 B2
(45) Date of Patent: Nov. 18, 2014

(54) BIOCATALYTIC PRODUCTION OF GLYCOSIDES

(75) Inventors: Giang Hai Tran, Ghent (BE); Tom Desmet, Nevele (BE); Wim Soetaert, Lovendegem (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 13/696,782

(22) PCT Filed: May 19, 2011

(86) PCT No.: PCT/EP2011/058177
§ 371 (c)(1),
(2), (4) Date: Nov. 7, 2012

(87) PCT Pub. No.: WO2011/144706
PCT Pub. Date: Nov. 24, 2011

(65) Prior Publication Data
US 2013/0059340 A1 Mar. 7, 2013

(30) Foreign Application Priority Data
May 21, 2010 (GB) .................................. 1008573.6

(51) Int. Cl.
  C12P 19/44 (2006.01)
  C12N 9/10 (2006.01)
  C12P 19/18 (2006.01)

(52) U.S. Cl.
  CPC ............... *C12N 9/1051* (2013.01); *C12P 19/18* (2013.01); *C12P 19/44* (2013.01); *C12Y 204/01049* (2013.01)
  USPC .............................................. 435/74; 435/72

(58) Field of Classification Search
None
See application file for complete search history.

(56) References Cited

U.S. PATENT DOCUMENTS

| 5,876,975 | A * | 3/1999 | Nakada et al. ................... 435/74 |
| 5,993,889 | A * | 11/1999 | Nakada et al. ................ 426/658 |
| 6,066,477 | A * | 5/2000 | Nishimoto et al. ............. 435/74 |
| 2007/0092949 | A1 * | 4/2007 | Odan et al. ..................... 435/101 |

OTHER PUBLICATIONS

Zhang et al., "Biosynthesis of radiolabeled cellodextrins by the *Clostridium thermocellum* cellobiose and cellodextrin phosphorylases for the measurement of intracellular sugars", Applied Microbiology and Biotechnology, vol. 70, pp. 123-129, 2006.*
Shintate et al., "Enzymatic synthesis of a library of beta-(1-4) hetero-D-glucose and D-xylose-based oligosaccharides employing cellodextrin phosphorylase", Carbohydrate Research, vol. 338, pp. 1981-1990, 2003.*

(Continued)

*Primary Examiner* — Rebecca Prouty
*Assistant Examiner* — Richard Ekstrom
(74) *Attorney, Agent, or Firm* — Knobbe, Martens, Olson & Bear LLP

(57) ABSTRACT

An in vitro method to produce a glycoside is described which includes the steps of contacting the cellodextrin phosphorylase from *Clostridium stercorarium* with alpha-glucose-1-phosphate or alpha-galactose-1-phosphate and an acceptor, and glycosylating the acceptor. The acceptor may be an alkyl beta-glucoside, an aryl beta-glucoside, a glucolipid, an alkyl beta-sophoroside, an aryl beta-sophoroside or a sophorolipid. Alkylcellobiosides, arylcellobiosides, cellobiolipids, cellotriolipids, glucosophorolipids and cellobiosesophorolipids are produced when alpha-glucose-1-phosphate is used as donor. Corresponding lactosides are produced when alpha-galactose-1-phosphate is used as donor.

15 Claims, 10 Drawing Sheets

1-O-Octyl-β-D-glucoside

4-Nitrophenyl β-D-glucoside

Glucolipid (GL)

(56) References Cited

OTHER PUBLICATIONS

Arai et al., "Purification and properties of cellodextrin phosphorylase from *Clostridium thermocellum*", Journal of Fermentation and Bioengineering, vol. 77, No. 3, pp. 239-242, 1994.*

Hiraishi, et al. "Synthesis of Highly Ordered Cellulose II in vitro Using Cellodextrin Phosphorylase," *Carbohydrate Research*, vol. 344, No. 18, pp. 2468-2473, Dec. 14, 2009.

Kawaguchi, et al. "Cloning, Nucleotide Sequence, and Expression of the *Clostridium thermocellum* Cellodextrin Phosphorylase Gene and Its Application to Synthesis of Cellulase Inhibitors," *Journal of Fermentation and Bioengineering*; vol. 85, No. 2, pp. 144-149, Jan. 1, 1998.

Nakai, et al. "Efficient Chemoenzymatic Oligosaccharide Synthesis by Reverse Phosphorolysis using Cellobiose Phosphorylase and Cellodextrin Phosphorylase from *Clostridium thermocellum*," *Biochimie*, vol. 92, No. 12, pp. 1818-1826, Dec. 1, 2010.

Reichenbecher, et al. :Purification and Properties of a Cellobiose Phosphorylase (CepA) and a Cellodextrin Phosphorylase (CepB) from the Cellulolytic Thermophile *Clostridium stercorarium, European Journal of Biochemsitry*, vol. 24, No. 1, pp. 262-267, Jul. 1, 1997.

Samain, et al. "Phosphorolytic Synthesis of Cellodextrins," *Carbohydrate Research*, vol. 271, No. 2, pp. 217-226, Jul. 11, 1995.

Sheth, et al. "Purification and Properties of $\beta$-1,4-Oligoglucan: Orthophosphate Glucosyltransferase from *Clostridium thermocellum*," *Journal of Biological Chemistry*, vol. 244, No. 2, pp. 457-464, Jan. 25, 1969.

Tran, et al. "Probing the Active Site of Cellodextrin Phosphorylase from *Clostridium stercorarium*: Kinetic Characterization, Ligand Docking, and Site-Directed Mutagenesis," *Biotechnology Progress*, vol. 27, No. 2, pp. 326-332, Feb. 21, 2011.

International Search Report dated Sep. 5, 2011, issued to priority international application No. PCT/EP2011/058177.

* cited by examiner

BIOCATALYTIC PRODUCTION OF GLYCOSIDES

CROSS-REFERENCE TO RELATED APPLICATIONS

This application is the U.S. National Phase under 35 U.S.C. §371 of International Application PCT/EP2011/058177, filed May 19, 2011, which claims priority to GB 1008573.6, filed May 21, 2010.

TECHNICAL FIELD OF INVENTION

The present invention relates to the biocatalytic production of glycosides. In particular, the invention discloses a method to produce alkylcellobiosides, arylcellobiosides, cellobiolipids, cellotriolipids, glucosophorolipids and cellobiosesophorolipids via the usage of a cellodextrin phosphorylase (CDP) derived from *Clostridium stercorarium* (CsCDP). The method of the present invention is feasible for use in industrial glycosylation processes and has advantageous properties compared to classical chemical glycosylation reactions. Moreover, said method can also be employed to produce corresponding lactosides such a lactolipids when α-galactose-1-phosphate instead of α-glucose-1-phosphate is used as a donor.

BACKGROUND ART

Alkylcellobiosides and arylcellobiosides have applications as chromogenic substrates or inhibitors of cellulases. Cellobioselipids, in turn, are high value products which are used as clean and biodegradable biosurfactants in detergent formulations. To date, these products are mainly synthesized via chemical or enzymatic glycosylation reactions.

Several chemical procedures have been described for the synthesis of glycosides. The most common procedures include the Fisher method and the Koenigs-Knorr method. However, the application of the Fisher method for synthesis of alkylbiosides is difficult because of concurrent alcoholysis of the interglycosidic linkage (Koto et al., 2004) and the Koenigs-Knorr method consists of a multi-step protocol that involves toxic intermediates and produces anomeric mixtures that need to be separated (Koto et al., 2004). Hence, the production of glycosides using classical chemical methods are laborious, have low yields and generate toxic waste.

Several publications describe the use of glycosylhydrolases (GHs) for the synthesis of glycosides (Basso et al., 2002; Gargouri et al., 2004). These enzymes are indeed interesting catalysts for enzymatic glycosylation as they have a relatively broad specificity. However, a major drawback is that they are not optimally suited for synthetic reactions, as their normal function is the breakdown (hydrolysis) of carbohydrates. Since the presence of water is necessary to maintain the enzymatic activity, but on the other hand causes substrate and product hydrolysis, the hydration level of the media has to be carefully controlled using solvents (Basso et al, 2002). As a result the obtained yields remain limited as glycosidases lose activity at low water activities.

Alternatively, glycosyltransferases can be used for glycosylation reactions. A major drawback, however, is that these enzymes require expensive nucleotide-activated carbohydrates (e.g. UDP-glucose) as glycosyldonor (Mendez & Salas, 2001; Fu et al., 2003). Consequently, this technology is likely to find application only for the targeted glycosylation of very high-value therapeutic proteins. Thus, the general industrial feasibility of using the latter enzymes for glycosylation reactions is very low. Hence, there is currently still a need to more efficiently produce glycosides such as alkylcellobiosides, arylcellobiosides and cellobioselipids at reduced cost and with a reduced environmental footprint.

Glycoside phosphorylases (GPs) catalyze the reversible breakdown of saccharide chains with the help of inorganic phosphate, resulting in a C1-phosphorylated monosaccharide and a saccharide of reduced chain length (Kitaoka et al., 2002). Because of the reversibility of this reaction, GPs can also be used for the synthesis of glycosidic bonds. In the synthetic direction, glucose-1-phosphate is used as donor and a hydroxylated compound as acceptor. The use of GPs for synthetic application has so far been explored by a limited number of groups. Most of them use GPs for the synthesis of rare carbohydrates. Kitao & Sekine (1992) have used sucrose phosphorylase with xylitol as the acceptor, resulting in the synthesis of glucosyl-xylitol. Aisaka et al. (2000) synthesised alpha-D-glucosyl-L-fucose using sucrose phosphorylase to transfer the glucosyl group from sucrose to L-fucose at position C-4. Okada et al. (2003) have recently described the synthesis of five novel oligosaccharides with kojibiose phosphorylase from *Thermoanaerobacter brockii*.

Cellodextrin phosphorylases are GPs that catalyze the reversible phosphorolysis of cellooligosaccharides into α-glucose-1-phosphate (Glc1P) and cellodextrins with reduced chain length (Kitaoka et al., 1992 and Kitaoka et al., 2002). They are involved in the degradation of cellulosic biomass in vivo. Only two CDPs have so far been described: one from *Clostridium stercorarium* and one from *Clostridium thermocellum*. Both enzymes are only 22% identical at the protein level. For the enzyme from *C. stercorarium*, solely the phosphorolysis of cello-oligosaccharides has been reported (Reichenberger et al., 1997). The enzyme from *C. thermocellum* has been characterised more thoroughly (Sheth 1969, Arai et al., 1994, Samain et al., 1995, Kawaguchi et al., and Sheth & Alexander, 1998) but glycosylation reactions with alkyl/aryl glucosides or glucolipids have not been reported.

The present invention discloses the finding that CsCDP shows a surprisingly high acceptor specificity for alkyl beta-glucosides, alkyl beta-sophorosides, aryl beta-glucosides, aryl beta-sophorosides, glucolipids and sophorolipids. Hence, the latter enzyme is useful to synthesize for example alkylcellobiosides, arylcellobiosides, cellobiolipids, cellotriolipids, glucosophorolipids and cellobiosophorolipids while overcoming the problems related to classical chemical or enzymatic glycosylation reactions to produce said products. In addition, the latter enzyme can also be employed to produce corresponding lactosides such as lactolipids when α-galactose-1-phosphate instead (Gal1P) of α-glucose-1-phosphate is used as a donor.

Figure 1:
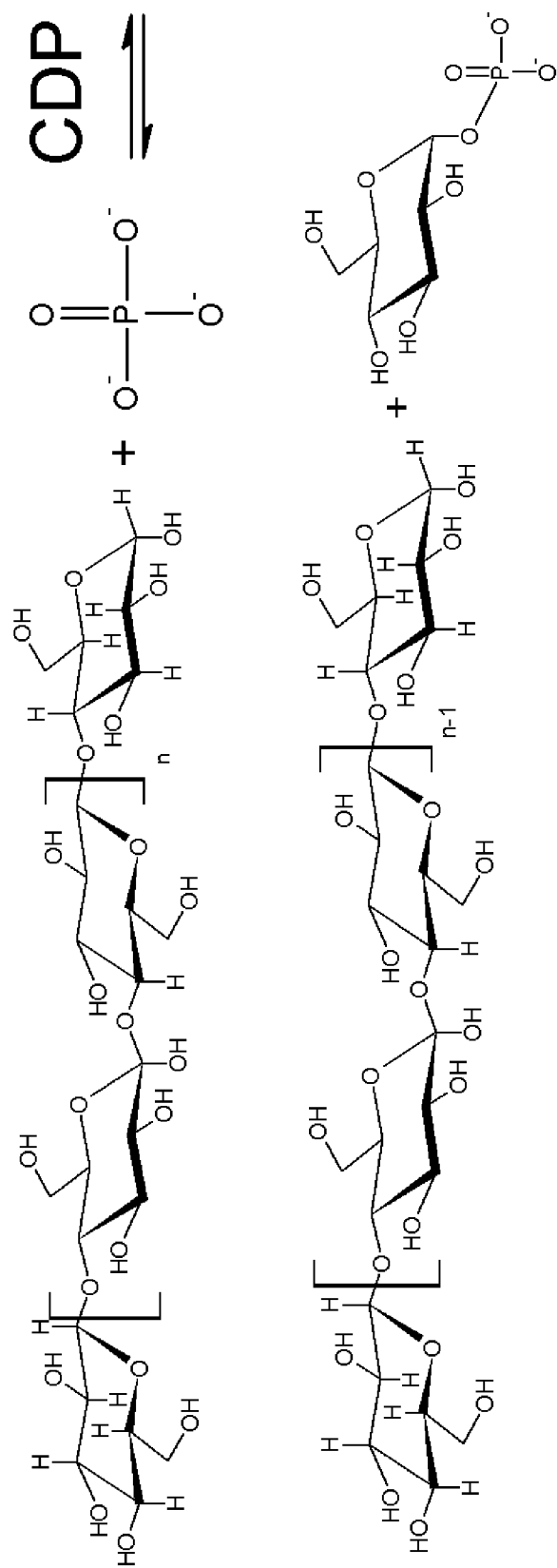
FIG. 1:
The Reaction Catalyzed by CDP

Production of novel glycolipids by CDP. (A) The transfer of glucose to glucolipids generates cellobio- and cellotriolipids, while (B) the transfer of galactose generates lactolipids. (C) glucosylation of sophorolipids results in gluco- and cellobiosophorolipids.

FIG. 6:

The yields of glycolipids produced by CDP. Reactions were performed at 45° C. and pH 6.5, using 20 mM of acceptor and either 30 mM Glc1P or 100 mM Gal1P as donor. Reaction of Gal1P with glucolipid (---) and of Glc1P with cellobiose (-), glucolipid (-..-) and sophorolipid (. . . ).

FIG. 7.

Chromatograms of the various glycolipids produced by CDP. Product purification was performed after the reaction of Glc1P with glucolipid (A), of Glc1P with sophorolipid (B), and of Gal1P with glucolipid (C). The masses of the products obtained by LC/MS are also shown.

DESCRIPTION OF INVENTION

The present invention concerns the surprising finding that the cellodextrin phosphorylase from *Clostridium stercorarium* (CsCDP) has a high specificity for the acceptors alkyl beta-glucosides, aryl beta-glucosides, alkyl beta-sophorosides, aryl beta-sophorosides, glucolipids and sophorolipids, and, for the donor galactose-1-phosphate. Moreover, the present invention demonstrates that said CsCDP can be used to efficiently synthesize or produce the corresponding glycosides such as—but not limited to—cellobiosides, cellobiolipids, cellotriolipids, glucosophorolipids, cellobiosophorolids and lactosides.

Hence, the present invention relates in first instance to a method to produce a glycoside comprising:
  contacting the cellodextrin phosphorylase from *Clostridium stercorarium* with glucose-1-phosphate and an acceptor, and
  glycosylating said acceptor,
  wherein said acceptor is an alkyl beta-glucoside, an aryl beta-glucoside, an alkyl beta-sophoroside, an aryl beta-sophoroside, a glucolipid or a sophorolipid.

The cellodextrin phosphorylase from *Clostridium stercorarium* (CsCDP) of the present invention refers to the CsCDP as described by Reichenberger et al. (1997) and can be obtained via any method known in the art. More in particular the present invention refers to the CsCDP encoded by the gene with Genbank number U60580 derived from *Clostridium stercorarium* strain DSM8532. The present invention further relates to a CsCDP which is a recombinantly expressed cellodextrin phosphorylase. For example, the gene encoding for the CsCDP of the present invention can be amplified by any means know in the art such as by PCR using an appropriate set of primers. The amplified gene or PCR product can then be ligated into any appropriate expression vector, such as for example the expression vector pTrc99a, which can be used to transform any appropriate host organism known in the art such as, for example, the bacterium *Escherichia coli* or the yeast *Candida albicans*. The enzyme produced by the host organism can then be extracted and purified by any method known in the art such as, for example, using an appropriate lysing buffer to extract intracellular CsCDP and a Ni-NTA gravity-flow column to purify His-tagged CsCDP. In this regard, it is clear that the invention further relates to a CsCDP which contains at least one deletion, substitution or addition, or any combination thereof, which does not diminish the glycosylating activity of said cellodextrin phosphorylase by at most 5%, 10%, 20%, 30%, 40% or 50%. In one embodiment, the CsCDP of the present invention contains at least one deletion, substitution or addition, or any combination thereof, which does not diminish the glycosylating activity of said cellodextrin phosphorylase by at most 50%. In other words, the present invention relates to a CsCDP which contains at least one deletion, substitution or addition, or any combination thereof, and which retains 95%, 90%, 80%, 70%, 60% or 50% of the glycosylating activity of the wild type cellodextrin phosphorylase. The glycosylating activity can be measured by any method known to a skilled person. A non-limiting example of an addition that does not influence the enzyme's activity is an N- or C-terminal addition of a His-tag.

The method of the present invention comprises 'contacting' the CsCDP of the present invention with an appropriate donor such as glucose-1-phosphate, or galactose-1-phosphate, and an appropriate acceptor such as an alkyl beta-glucoside, an aryl beta-glucoside, an alkyl beta-sophoroside, an aryl beta-sophoroside, a glucolipid or a sophorolipid. The latter 'contacting' can occur by bringing together an appropriate amount of enzyme, donor and acceptor in an appropriate buffer such as 50 mM MES buffer having a pH of 6.5 in order to produce the cellobiosides, cellobiolipids, cellotriolipids, glucosophorolipids, cellobiosophorolids and lactosides of the present invention, or, can occur, especially with regard to the production of cellobiolipids, cellotriolipids, glucosophorolipids and cellobiosophorolids, inside an appropriate host cell, such as a yeast cell, which recombinantly expresses the CsCDP of the present invention. Hence the present invention relates to a method as described above to produce a cellobiolipid, a cellotriolipid, a glucosophorolipid or a cellobiosophorolid by a yeast cell which recombinantly expresses cellodextrin phosphorylase. Said yeast preferably belongs to the genus *Candida*.

The enzyme of the method of the present invention displays a surprisingly high activity towards alkyl beta-glucosides such as methyl-, ethyl-, butyl-, pentyl, hexyl-, heptyl-, octyl-, nonyl-, decyl-, undecyl- and dodecyl beta-glucosides, arylglucosides such p-nitrophenyl beta-glucoside, glucolipids such as oleoyl beta-glucoside or sophorolipids such as oleoyl beta-sophorolipid. Therefore, the present invention relates to a method according to the present invention wherein said alkylglucoside is a methyl to dodecyl beta-glucoside, wherein said arylglucoside is a p-nitrophenyl beta-glucoside, wherein said glucolipid is oleoyl beta-glucoside or wherein said sophorolipid is an oleoyl beta-sophorolipid.

The latter method preferably relates to a method according to the present invention wherein said alkyl beta-glucoside is a methyl-, hexyl- or octyl beta-glucoside.

The method of the invention more specifically relates to a method to produce glycosides wherein said glycoside is an alkylcellobioside, an arylcellobioside, a cellobiolipid, a cellotriolipid, a glucosophorolipid or a cellobiosophorolid.

As the present invention further relates to the surprising finding that CsCDP is active on alpha-galactose-1-phosphate as donor substrate instead of alpha-glucose-1-phosphate, the method of the present inventions further relates to a method wherein said glucose-1-phosphate is replaced by galactose-1-phosphate and, more specifically, wherein said cellobiolipid is replaced by a corresponding lactolipid.

The present invention will now be illustrated by the following non-limiting examples.

EXAMPLES

Materials and Methods

Reagents

All primers (Table 1) and chemicals were purchased from Sigma, except for cellobiose and methyl, hexyl and octyl β-glucosides (Carbosynth). The glucolipid oleoyl β-glucoside and the sophorolipid oleoyl β-sophoroside were produced as described previously (Saerens et al., 2009). The sequence of the enzymes was checked at the AGOWA service facility (www.agowa.de).

TABLE 1

List of the primers used in this study

Primer sequences

1  CsCDP-F: 5'-gagctcatgcgttacggttattttgatg-3'          (SEQ ID No. 1)
   CsCDP-R: 5'-gtcgactcatccattataacaacacattcac-3'       (SEQ ID No. 2)

2  CsCDP-His-F: 5'-cacacaggaaacagaccatgcaccatcaccatcaccatcgttacgg-3' (SEQ ID No. 3)
   CsCDP-His-R: 5'-ccgtaacgatggtgatggtgatggtgcatggtctgtttcctgtgtg-3' (SEQ ID No. 4)

Cloning and Expressing CsCDP

The genomic DNA of *C. stercorarium* DSM8532 was ordered from the Deutsche Sammlung von Mikroorganismen and Zellkulturen (DSMZ). The CsCDP gene (Genbank U60580 SEQ ID No. 5, encoding the amino acid sequence of SEQ ID No. 6) was amplified by means of PCR, using primer pair 1 (Table 1). The PCR product was then ligated into the expression vector pTrc99a. Subsequently, six histidine residues were introduced at the N-terminus with the Quick-Change XL II Site Directed Mutagenesis kit (Stratagene), using primer pair 2 (Table 1).

The expression plasmids were used to transform to an expression *E. coli* host strain BL21 (Stratagene) by a heat-shock treatment. Expression was induced by 0.01 mM IPTG when $A_{600}$ reached 0.6 in Luria Broth medium at 37° C. The *E. coli* cells were harvested by centrifugation after four hours of expression.

The intracellular CsCDP was extracted from frozen pellets by a lysis buffer containing 50 mM $NaH_2PO_4$, 300 mM NaCl and 1 mg/mL lysozyme at pH 8.0. The CsCDP was purified from the crude extract via a Ni-NTA gravity-flow column (Qiagen). The His-tagged CsCDP was then eluted with a buffer containing 50 mM $NaH_2PO_4$, 300 mM NaCl and 250 mM imidazole, pH 8.0 which was subsequently eliminated and replaced by a 50 mM MES buffer pH 6.5, via a Microcon YM-30 (Millipore). The purity of the enzymes was checked by SDS-PAGE, using the LMW-SDS Marker Kit from GE Healthcare as the standard.

Assay Methods

Protein concentrations were measured with the BCA Protein Assay kit from Thermo Scientific. The activity assays were performed with 5% of purified enzyme (50 μg/mL, final concentration) in 50 mM MES buffer pH 6.5, containing 30 mM donor (Glc1P) or 100 mM donor (Gal1P) and 50 mM acceptor at 45° C. Samples were inactivated for 5 minutes at 95° C. before the amount of orthophosphate ($P_i$) was measured by the method of Gawronski and Benson, 2004. The $K_m$ and $k_{cat}$ values in the kinetic study were calculated from a Hanes-Woolf plot.

Results

1. Characterization of the Cellodextrin Phosphorylase from *Clostridium stercorarium*

Figure 2:
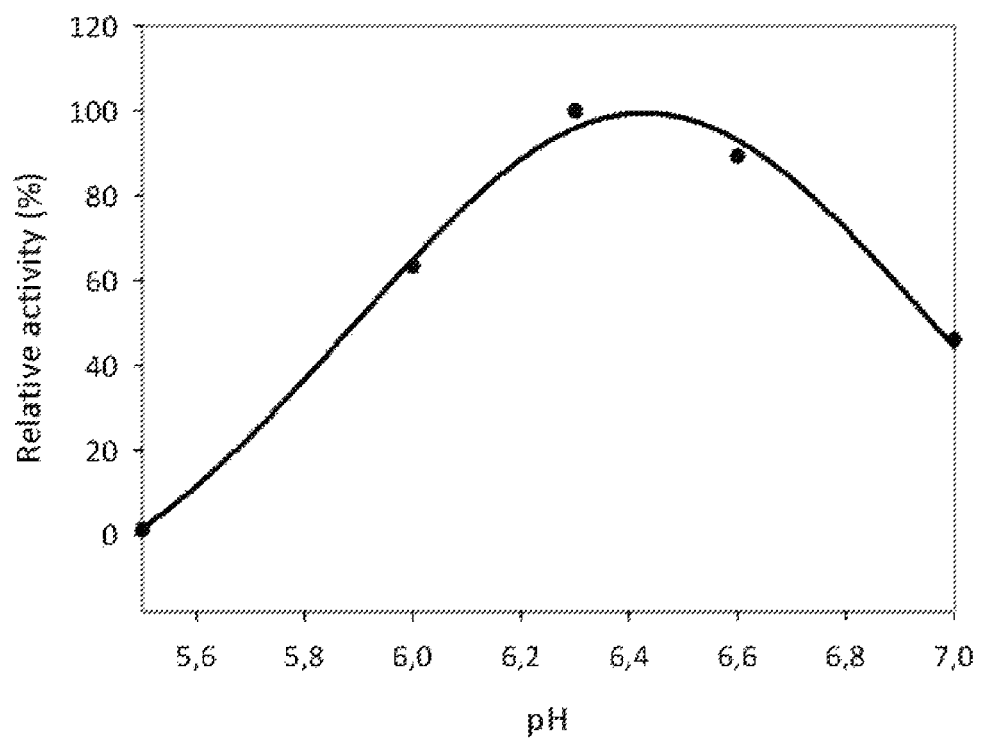
FIG. 2:
Effect of pH on the Wild-Type Activity of Recombinant CsCDP
The reaction was performed with 50 mM cellobiose and 30 mM Glc1P in 50 mM MES buffer at 45° C.
Figure 3:
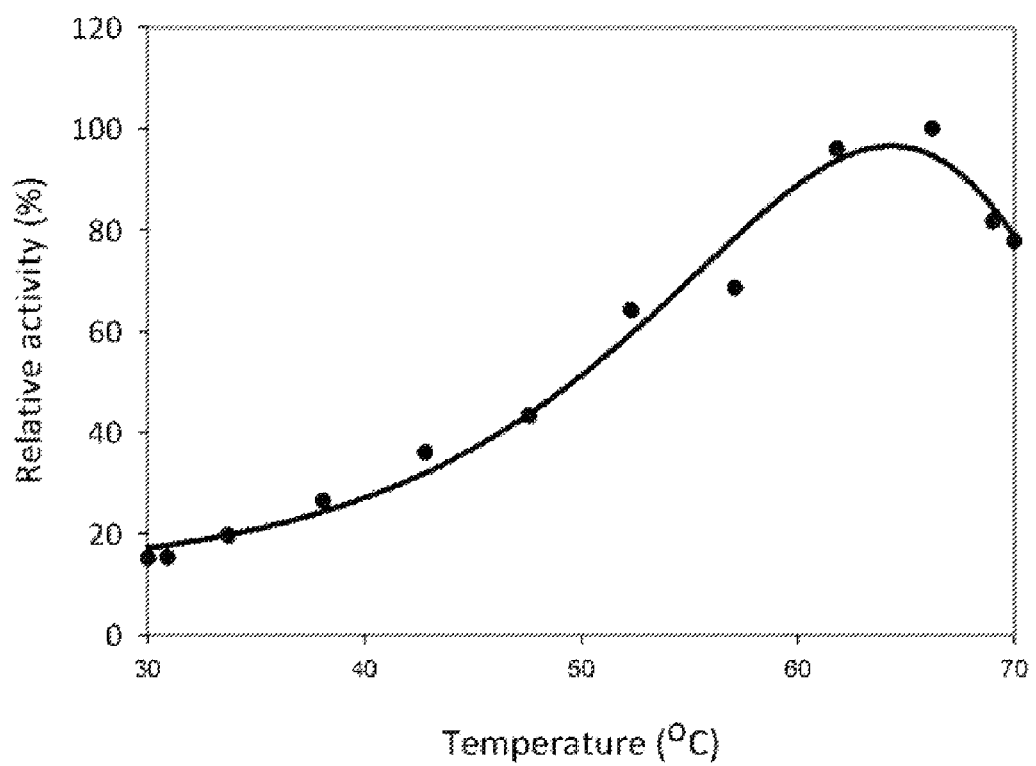
FIG. 3:
Effect of Temperature on the Wild-Type Activity of Recombinant CsCDP
The reaction was performed with 50 mM cellobiose and 30 mM Glc1P in 50 mM MES buffer pH 6.5.

In this study, heterologous expression of CsCDP in *E. coli* has been achieved for the first time. The $His_6$-tagged purified CsCDP had a specific activity of 22.4 U/mg and gave a single band around 91 kDa on SDS-PAGE, which corresponds well with the theoretical molecular mass of 91.497 kDa. The optimal pH and temperature for the enzyme's activity in the direction of glycoside synthesis were found to be around 6.5 and 65° C., respectively (FIGS. 2 and 3), comparable to previously published results (Reichenbecher et al., 1997).

Figure 4:
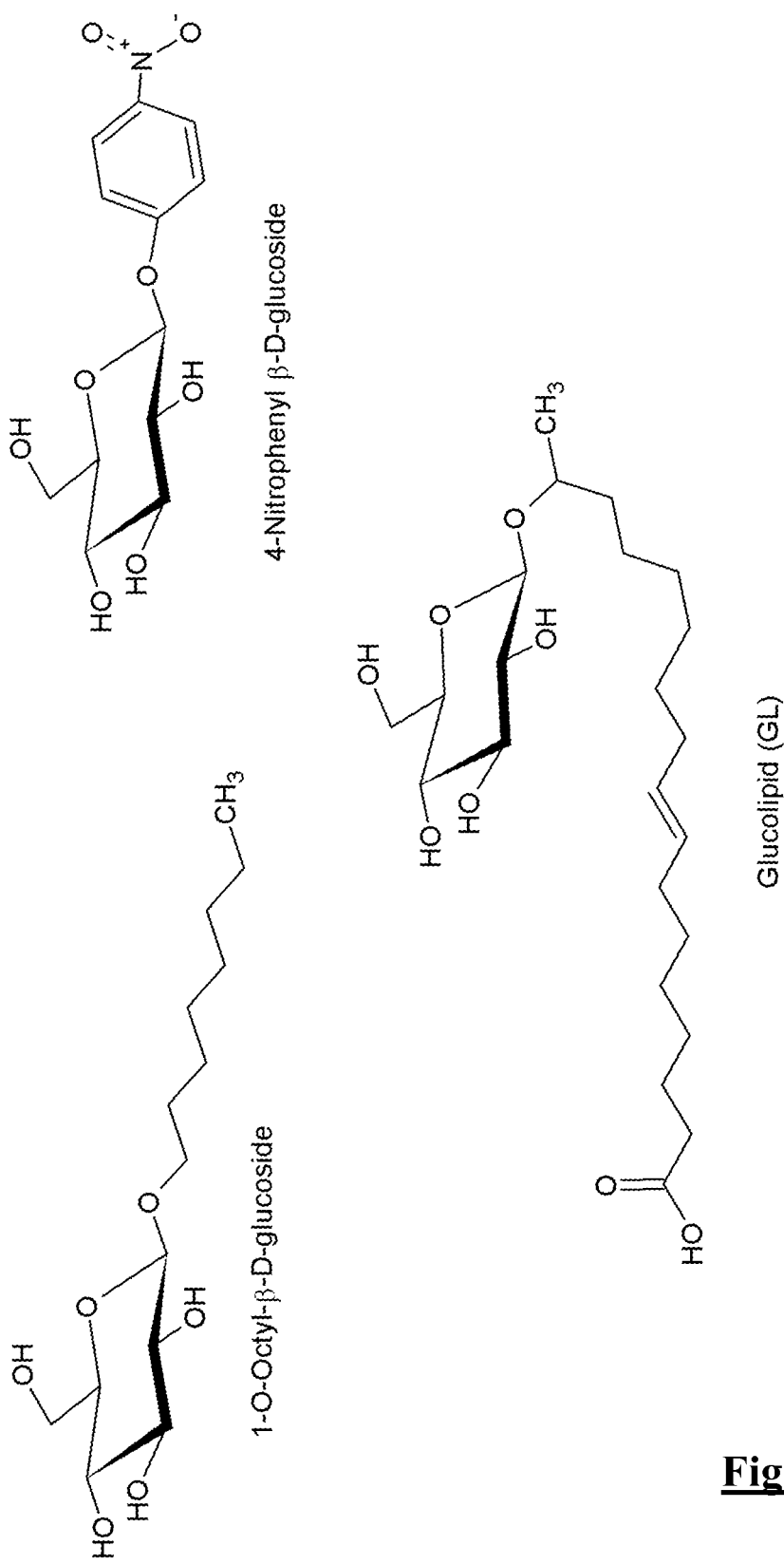
FIG. 4:
The Structure of the Most Interesting Acceptors for CsCDP

The substrate specificity of CsCDP was examined with 11 different acceptor molecules (Table 2). The structures of the most interesting ones are illustrated in FIG. 4. The enzyme was found to display high activity towards aryl and alkyl β-glucosides as well as glucolipids. Indeed, a p-nitrophenyl (PNP) or octyl chain and especially an oleoyl tail seem to bind as efficiently as a glucosyl moiety in subsite +2. Disaccharides containing an α-glucosidic linkage (maltose, sucrose) are very poor acceptors, but the only acceptor on which absolutely no activity could be detected, was lactose. The latter molecule only differs from cellobiose in the orientation of the C4'-hydroxyl group, which is the point of attachment for the glycosidic bond.

TABLE 2

Acceptor specificity of CsCDP

| Substrate | Specific activity (U/mg) | Relative activity (%) |
|---|---|---|
| Cellobiose | 22.4 | 100 |
| Glucose | 0.6 | 2 |
| Methyl β-glucoside | 3.5 | 16 |
| Hexyl β-glucoside | 19.9 | 89 |
| Octyl β-glucoside | 20.4 | 91 |
| Oleoyl β-glucoside | 29.3 | 131 |
| PNP β-glucoside | 24.7 | 110 |
| PNP β-cellobioside | 29.0 | 129 |
| PNP β-xyloside | 7.5 | 33 |
| Maltose | 0.7 | 3 |
| Sucrose | 0.7 | 3 |
| Lactose | — | — |

The reaction was performed at 45° C. in 50 mM MES buffer pH 6.5, using 50 mM of acceptor. (PNP = p-nitrophenyl)

The substrate specificity of CsCDP was examined in more detail by determining the kinetic parameters for selected molecules (Table 3). In general, the $K_m$ values of CsCDP for both cellobiose and Glc1P are much lower than those of the CDP from *C. thermocellum* (Sheth and Alexander 1969). Surprisingly, the enzyme was also found to be active on α-galactose-1-phosphate (Gal1P) as donor substrate instead of α-glucose-1-phosphate (Glc1P). However, its efficiency on this substrate is about one thousand times lower, as both the activity and the affinity are drastically reduced.

TABLE 3

Kinetic parameters for the synthetic reaction of CsCDP

| | $K_m$ (μM) | $k_{cat}$ (s$^{-1}$) | $k_{cat}/K_m$ (μM$^{-1}$s$^{-1}$) |
|---|---|---|---|
| Glc1P | 2438 ± 16 | 27.4 ± 1.7 | 0.01 |
| Gal1P | 31130 ± 683 | 2.5 ± 0.1 | 0.0001 |
| Cellobiose | 447 ± 5 | 18.1 ± 0.5 | 0.04 |
| Octyl β-glucoside | 623 ± 26 | 14.2 ± 0.5 | 0.02 |
| PNP β-glucoside | 640 ± 38 | 19.6 ± 1.0 | 0.03 |

The reaction was performed in 50 mM MES buffer pH 6.5 at 45° C.

2. Production of Glycolipids with Cellodextrin Phosphorylase

Figure 5:
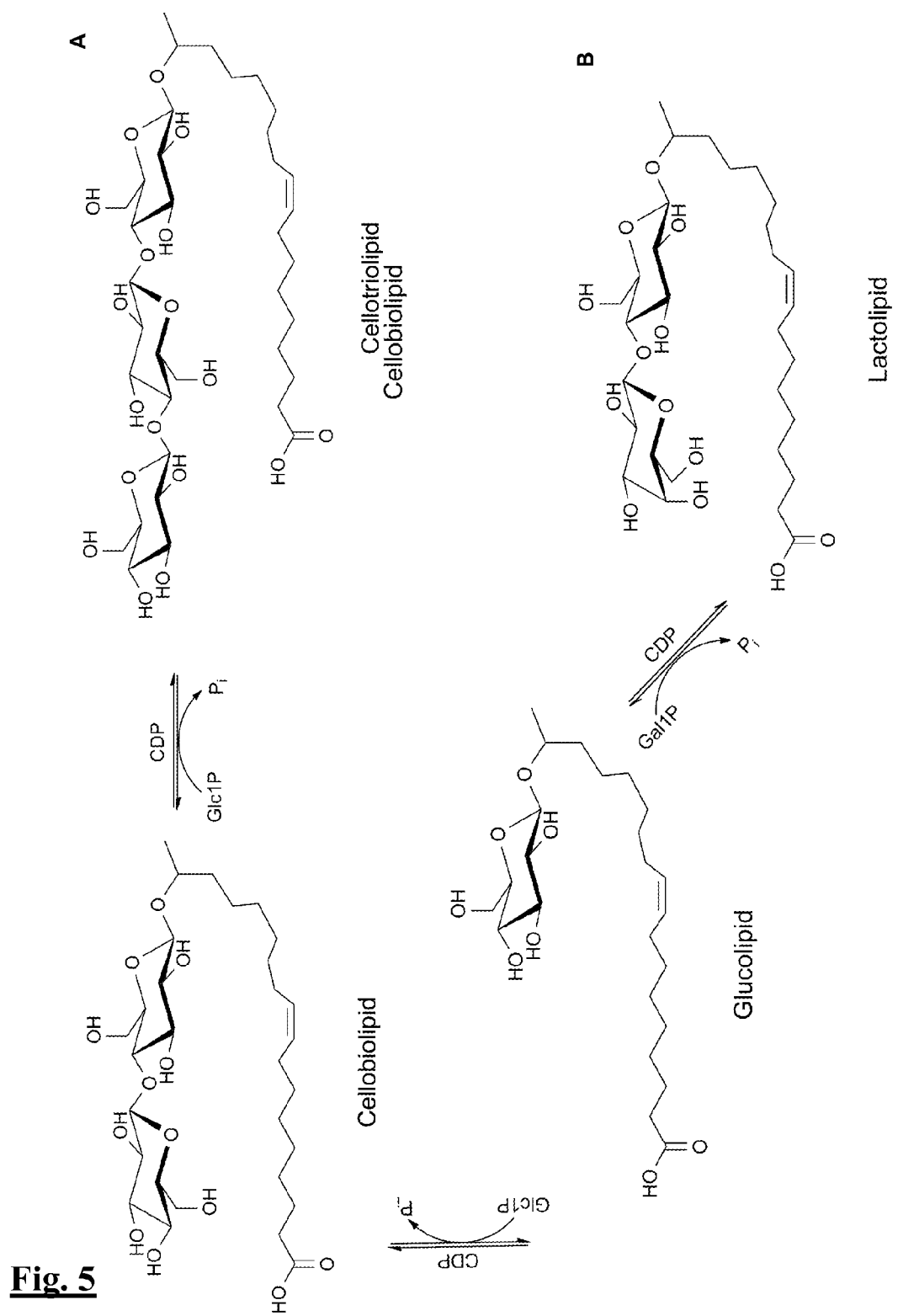
FIG. 5.
Figure 5:
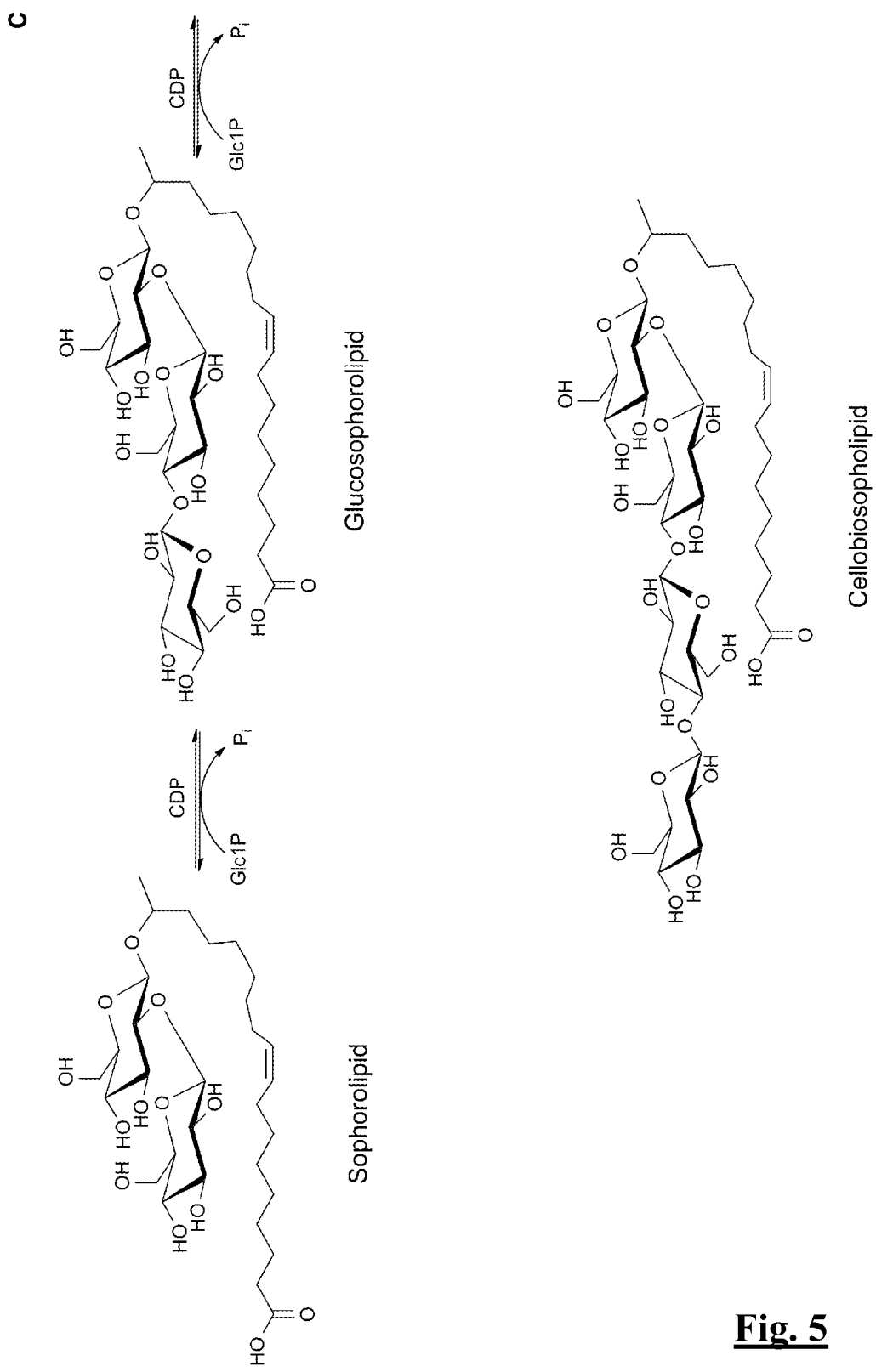

While glucolipids were found to be better acceptors for CDP than cellobiose, sophorolipids generated an activity that is about one third of that on cellobiose (Table 4). Interestingly, the products formed by the glucosylation of sophoro- and glucolipids were found to also serve as acceptors for CDP, resulting in the formation of products with additional glucose moieties (FIG. 5) (see further). Unfortunately, the rate of this second glucosylation step could not be determined because the intermediate compounds are not available in purified form. When Gal1P is used as donor, however, only a single product is formed. This is consistent with the finding that CDP is inactive towards lactose as acceptor (Table 2).

TABLE 4

Glycolipid production by CDP at 45° C. and pH 6.5*

| Donor | Acceptor | Activity (%)# | Product | Solubility | Yield (%)$ |
|---|---|---|---|---|---|
| Glc1P | Cellobiose | 100 | Cello-oligosaccharide | + | 50 |
| Glc1P | Glucolipid | 126 | Cellobiolipid | − | 80 |
| | | | Cellotriolipid | − | 55 |
| Glc1P | Sophorolipid | 36 | Glucosophorolipid | − | 75 |
| | | | Cellobiosophorolipid | − | 50 |
| Gal1P | Glucolipid | 11 | Lactolipid | + | 50 |

Figure 6:
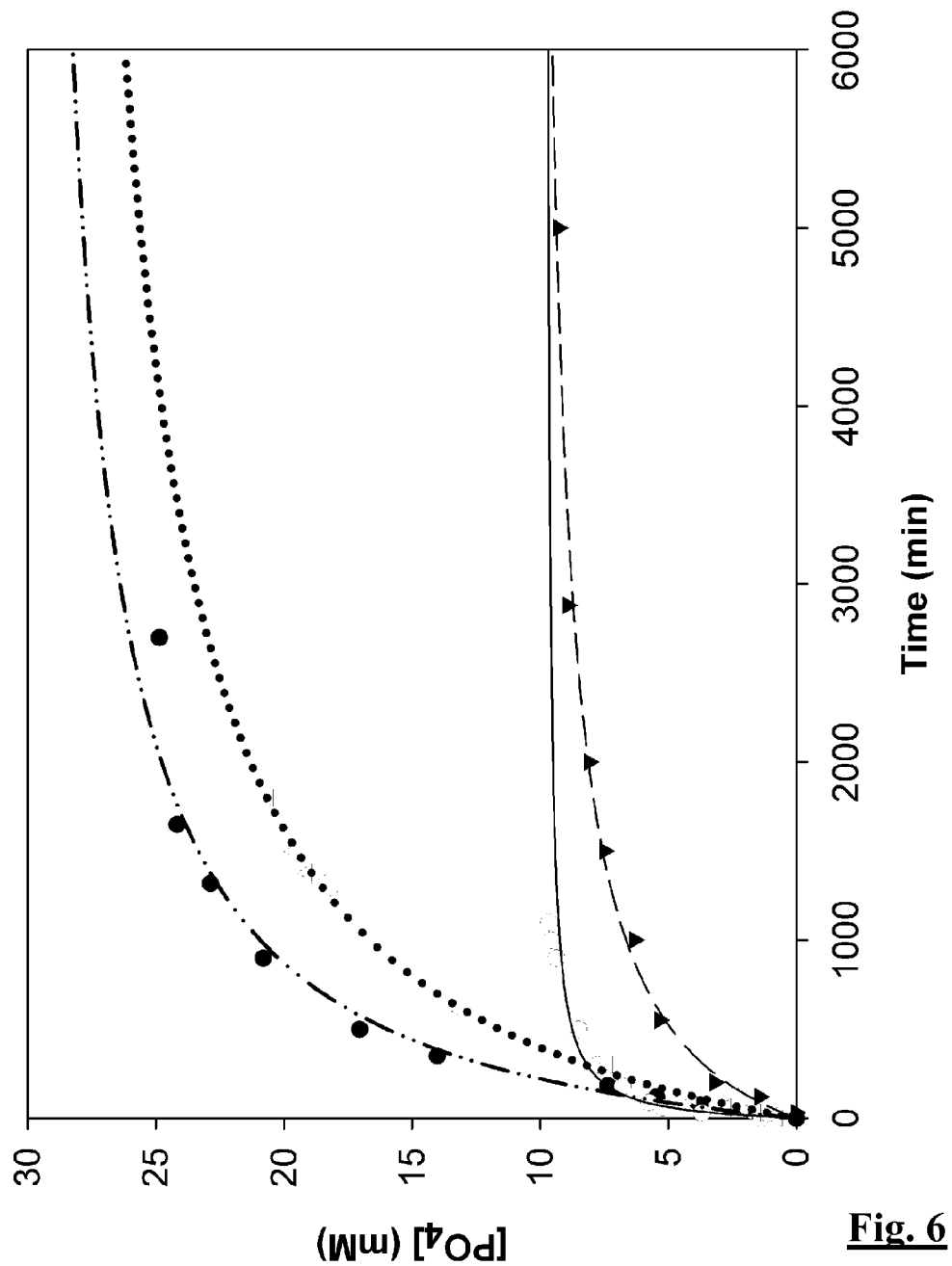

*using 20 mM of acceptor and either 30 mM Glc1P or 100 mM Gal1P as donor
relative to the activity on cellobiose,
$relative to the acceptor concentration As phosphorylases catalyse a reversible reaction, complete conversion of the substrate is difficult to achieve and product yields of about 30-70% are typically obtained at equilibrium. To determine the yields of the new glycolipids produced by CDP, the conversion of the acceptor substrates has been monitored until apparent equilibrium. When 20 mM cellobiose was used as acceptor, maximally 10 mM of inorganic phosphate was released from the donor Glc1P, indicating a conversion of about 50% (FIG. 6). In contrast, when gluco- or sophorolipids were used at a similar concentration, up to 27 and 25 mM of phosphate, respectively, was generated. Indeed, the glucosylated products can serve as acceptor for a second reaction, resulting in additional consumption of the glycosyl donor (starting concentration of 30 mM). Furthermore, the products were found to be insoluble, forming a white precipitate in the reaction mixture. Such behaviour drives the reaction to completion, until almost no glycosyl donor is available any more. This is not the case when Gal1P is employed as glycosyl donor (starting concentration of 100 mM), as this generates just a single product that remains in solution. Consequently, a yield of only 50% is obtained for the galactosylated lipids (FIG. 6).

Figure 7:
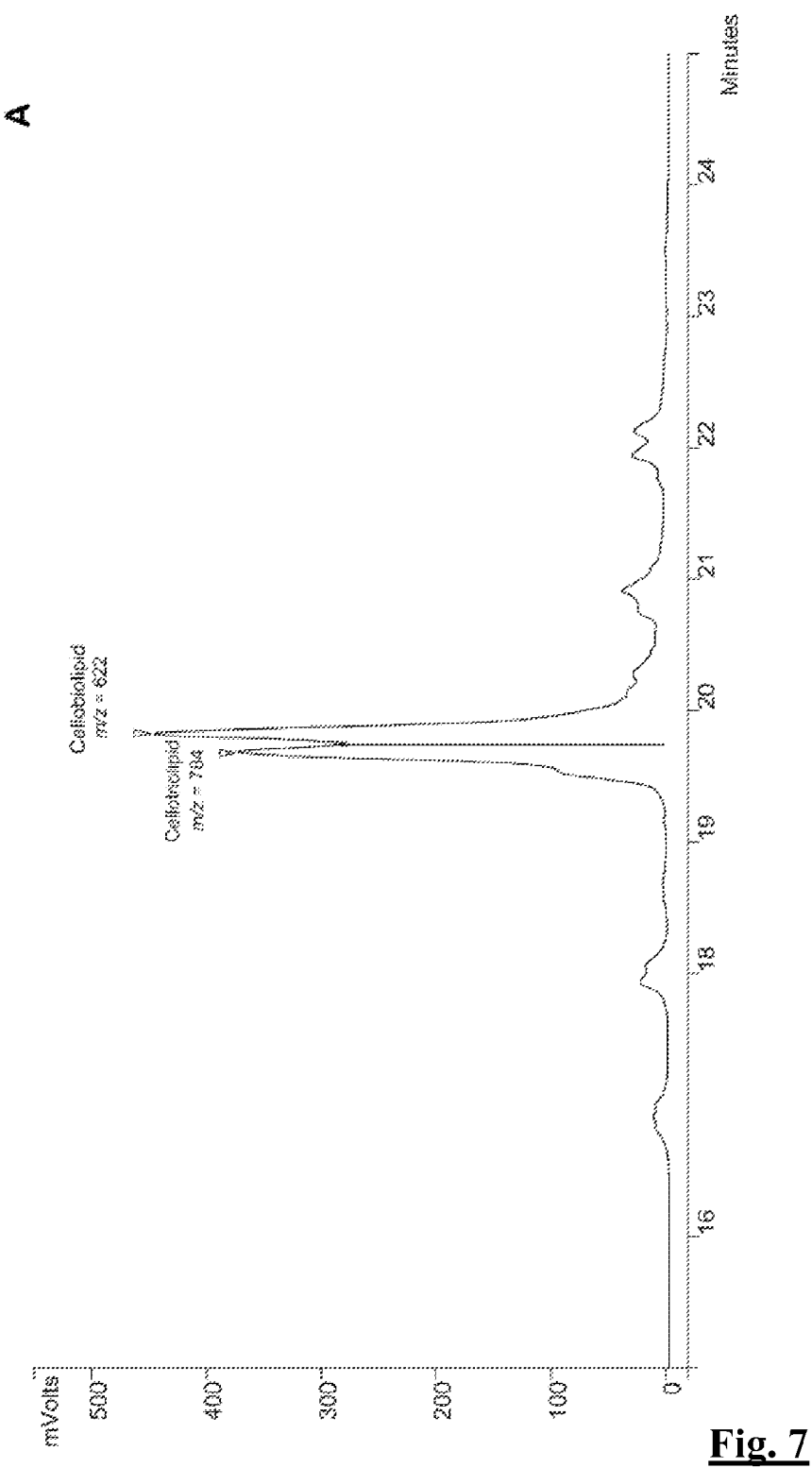
Figure 7:
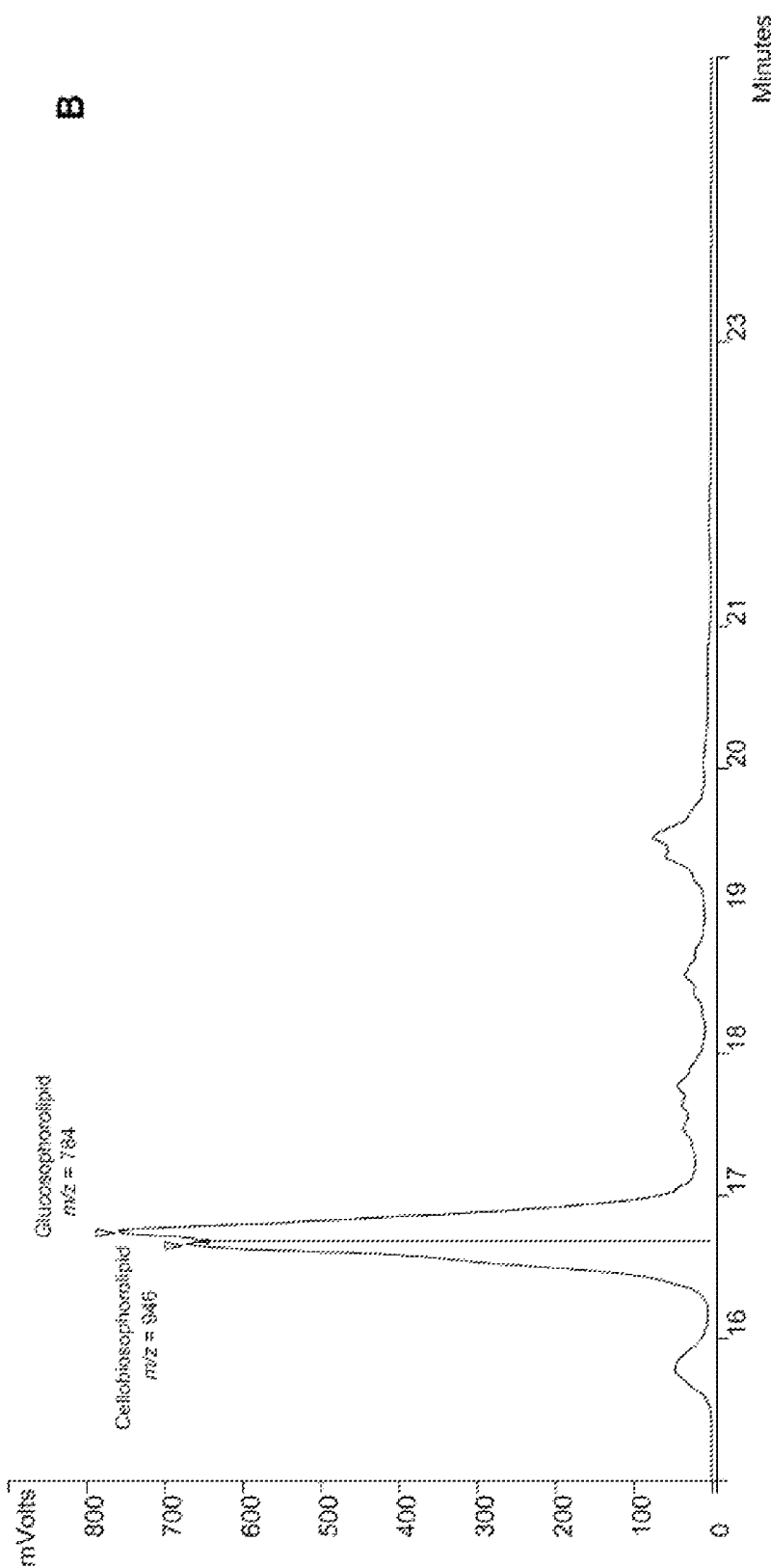
Figure 7:
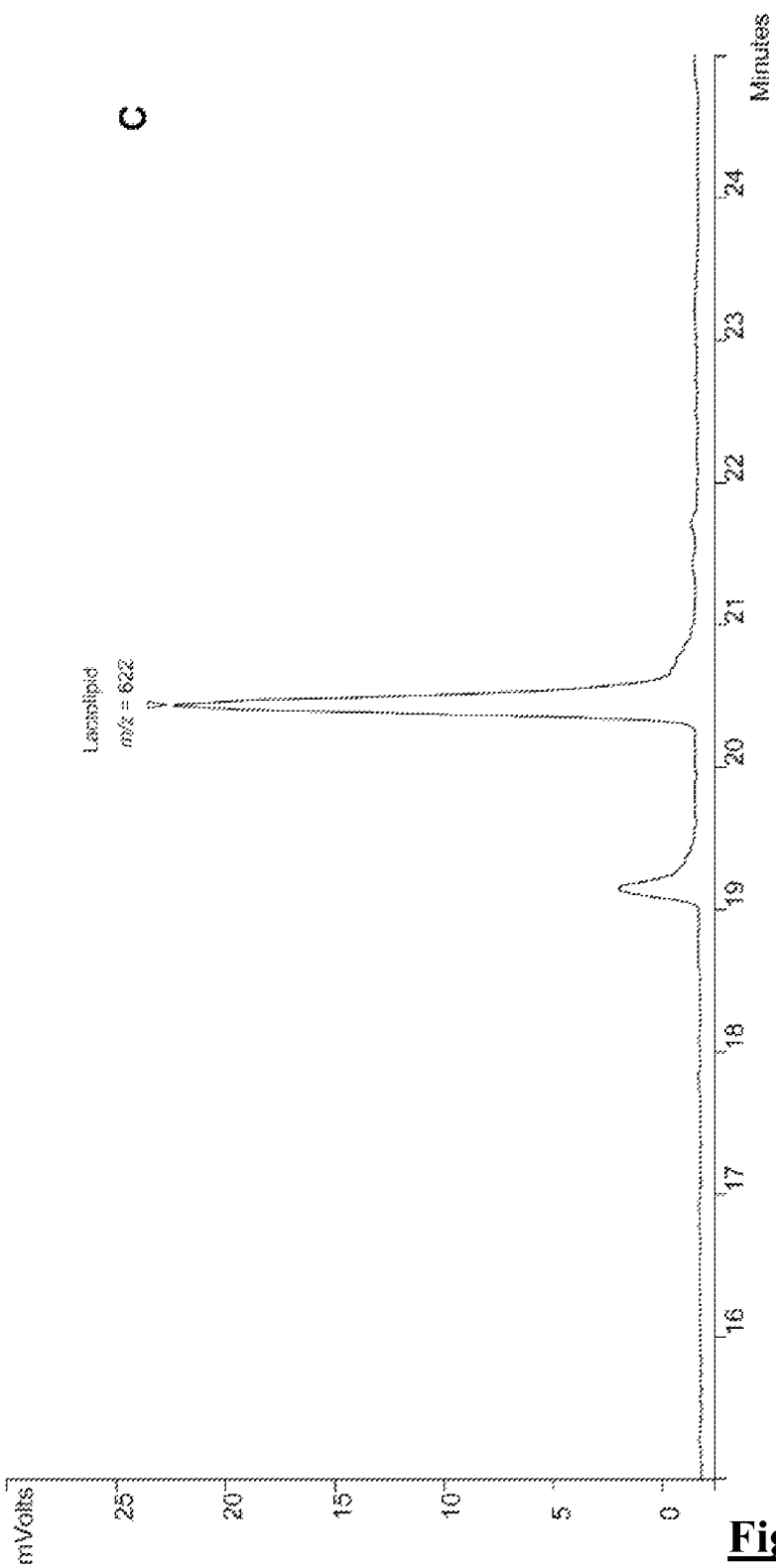

The precipitation of the glucosylated reaction products greatly facilitated their purification, as they could be simple recovered by centrifugation. Washing the pellets with water and ethyl acetate helped to remove trace amounts of donor and acceptor, respectively. Analysis by HPLC revealed that the products of the initial and subsequent glucosylation reactions are present in a ratio of 3/2 (Table 4). The products of the reaction with glucolipid acceptors have been designated as cellobio- and cellotriolipids, while those of the reaction with sophorolipid acceptors will be called gluco- and cellobiosophorolipids. The degree of glycosylation has been confirmed by MS-analysis, which clearly demonstrated the stepwise addition of two glycosyl groups (FIG. 7). The purification of the galactosylated product was somewhat more complicated and required two extraction steps. First, the remaining acceptor substrate (glucolipid) was removed by depurating with ethyl acetate. After decanting, the pH of the solution was lowered to 2, which caused the product to migrate to the solvent phase during a second extraction step. In that way, it could be effectively separated from the remaining donor in the aqueous phase. In the chromatogram, only one product peak is observed (FIG. 7) of which the mass corresponds perfectly with that of a lactolipid.

REFERENCES

Aisaka, K., T. Masuda-Kato, T. Chikamune, K. Kamitori, Y. Uosaki and Y. Saito (2000). "Enzymatic synthesis of novel disaccharides using disaccharide phosphorylases." *Journal of Bioscience and Bioengineering* 90(2): 208-213.

Arai, M., K. Tanaka and T. Kawaguchi (1994). "Purification and properties of cellodextrin phosphorylase from *Clostridium thermocellum*." *Journal of Fermentation and Bioengineering* 77(3): 239-242.

Basso, A., A. Ducret, L. Gardossi and R. Lortie (2002). "Synthesis of octyl glucopyranoside by almond [beta]-glucosidase adsorbed onto Celite R-640®." *Tetrahedron Letters* 43(11): 2005-2008.

Fu, X., Albermann, C., Jiang, J., Liao, J., Zhang, C. & Thorson, J. S. (2003). Antibiotic optimization via in vitro glycorandomization. Nature Biotechnology, 21, 1467-1469.

Gargouri, M., I. Smaali, T. Maugard, M. D. Legoy and N. Marzouki (2004). "Fungus [beta]-glycosidases: immobilization and use in alkyl-[beta]-glycoside synthesis." *Journal of Molecular Catalysis B: Enzymatic* 29(1-6): 89-94.

Gawronski, J. D. and D. R. Benson (2004). "Microtiter assay for glutamine synthetase biosynthetic activity using inorganic phosphate detection." *Analytical biochemistry* 327 (1): 114-118.

Kawaguchi, T., Y. Ikeuchi, N. Tsutsumi, A. Kan, J. I. Sumitani and M. Arai (1998). "Cloning, nucleotide sequence, and expression of the *Clostridium thermocellum* cellodextrin phosphorylase gene and its application to synthesis of cellulase inhibitors." *Journal of Fermentation and Bioengineering* 85: 144-149.

Kitao, S. and H. Sekine (1992). "Transglucosylation Catalyzed by Sucrose Phosphorylase from *Leuconostoc mesenteroides* and Production of Glucosyl-xylitol." *Bioscience, biotechnology, and biochemistry* 56(12): 2011-2014 Kitaoka, M. and K. Hayashi (2002). "Carbohydrate-processing phosphorolytic enzymes." *Trends in Glycoscience and Glycotechnology* 14: 33-50.

Kitaoka, M., T. Sasaki and H. Taniguchi (1992). "Synthetic reaction of *Cellvibrio gilvus* cellobiose phosphorylase." *J Biochem* 112(1): 40-44.

Koto, S., M. Hirooka, T. Tashiro, M. Sakashita, M. Hatachi, T. Kono, M. Shimizu, N. Yoshida, S. Kurasawa, N. Sakuma, S. Sawazaki, A. Takeuchi, N. Shoya and E. Nakamura (2004). "Simple preparations of alkyl and cycloalkyl [alpha]-glycosides of maltose, cellobiose, and lactose." *Carbohydrate Research* 339(14): 2415-2424.

Méndez, C. and J. A. Salas (2001). "Altering the glycosylation pattern of bioactive compounds." *Trends in Biotechnology* 19(11): 449-456.

Okada, H., E. Fukushi, S. Onodera, T. Nishimoto, J. Kawabata, M. Kikuchi and N. Shiomi (2003). "Synthesis and structural analysis of five novel oligosaccharides prepared by glucosyltransfer from [beta]-glucose 1-phosphate to isokestose and nystose using *Thermoanaerobacter brockii* kojibiose phosphorylase." *Carbohydrate Research* 338(9): 879-885.

Reichenbecher, M., F. Lottspeich and K. Bronnenmeier (1997). "Purification and properties of a Cellobiose Phosphorylase (CepA) and a Cellodextrin Phosphorylase (CepB) from the cellulolytic thermophile *Clostridium stercorarium*." *European Journal of Biochemistry* 247(1): 262-267.

Saerens, K., I. V. Bogaert, W. Soetaert and E. Vandamme (2009). "Production of glucolipids and specialty fatty acids from sophorolipids by *Penicillium decumbens naringinase*: Optimization and kinetics." *Biotechnology Journal* 4(4): 517-524.

Samain, E., C. Lancelon-Pin, F. Ferigo, V. Moreau, H. Chanzy, A. Heyraud and H. Driguez (1995). "Phosphorolytic synthesis of cellodextrins." *Carbohydrate Research* 271(2): 217-226.

Sheth, K. and J. K. Alexander (1969). "Purification and properties of β-1,4-Oligoglucan: Orthophosphate Glucosyltransferase from *Clostridium thermocellum*." *Journal of Biological Chemistry* 244(2): 457-464.

What is claimed is:

1. An in vitro method to produce a glycoside comprising: contacting in vitro the cellodextrin phosphorylase from *Clostridium stercorarium* with alpha-glucose-1-phosphate and an acceptor, and glycosylating said acceptor, wherein said acceptor is an alkyl beta-glucoside, an aryl beta-glucoside, a glucolipid, an alkyl beta-sophoroside, an aryl beta-sophoroside or a sophorolipid.

2. A method according to claim 1 wherein said cellodextrin phosphorylase from *Clostridium stercorarium* is encoded by a nucleic acid having the sequence shown as SEQ ID NO: 5.

3. A method according to claim 1, wherein said cellodextrin phosphorylase is a recombinantly expressed cellodextrin phosphorylase.

4. A method according to claim 1, wherein said alkyl beta-glucoside is a methyl to dodecyl beta-glucoside, wherein said aryl beta-glucoside is a p-nitrophenyl beta-glucoside, wherein said glucolipid is oleoyl beta-glucoside or wherein said sophorolipid is an oleoyl beta-sophorolipid.

5. A method according to claim 4 wherein said alkyl beta-glucoside is a methyl-, hexyl- or octyl beta-glucoside.

6. A method according to claim 1, wherein said glycoside is an alkylcellobioside, an arylcellobioside, a cellobiolipid, a cellotriolipid, a glucosophorolipid or a cellobiosophorolipid.

7. An in vitro method to produce a glycoside comprising: contacting the cellodextrin phosphorylase from *Clostridium stercorarium* with alpha galactose-1-phosphate and an acceptor in vitro, and glycosylating said acceptor, wherein said acceptor is an alkyl beta-glucoside, an aryl beta-glucoside, a glucolipid, an alkyl beta-sophoroside, an aryl beta-sophoroside or a sophorolipid.

8. A method according to claim 7 wherein said glycoside is a lactolipid.

9. A method according to claim 7, wherein said cellodextrin phosphorylase from *Clostridium stercorarium* is encoded by a nucleic acid having the sequence shown as SEQ ID NO: 5.

10. A method according to claim 7, wherein said cellodextrin phosphorylase is a recombinantly expressed cellodextrin phosphorylase.

11. A method according to claim 7, wherein said alkyl beta-glucoside is a methyl to dodecyl beta-glucoside, wherein said aryl beta-glucoside is a p-nitrophenyl beta-glucoside, wherein said glucolipid is oleoyl beta-glucoside or wherein said sophorolipid is an oleoyl beta-sophorolipid.

12. A method according to claim 11 wherein said alkyl beta-glucoside is a methyl-, hexyl- or octyl beta-glucoside.

13. A method according to claim 7, wherein said glycoside is an alkylcellobioside, an arylcellobioside, a cellobiolipid, a cellotriolipid, a glucosophorolipid or a cellobiosophorolipid.

14. The method of claim 1, wherein the aryl beta-sophoroside is a p-nitrophenyl beta-sophoroside.

15. The method of claim 6, wherein the arylcellobioside is p-nitrophenylcellobioside.

* * * * *

SEQUENCE LISTING

```
<160> NUMBER OF SEQ ID NOS: 6

<210> SEQ ID NO 1
<211> LENGTH: 28
<212> TYPE: DNA
<213> ORGANISM: Artificial
<220> FEATURE:
<223> OTHER INFORMATION: synthesized

<400> SEQUENCE: 1
gagctcatgc gttacggtta ttttgatg                                          28

<210> SEQ ID NO 2
<211> LENGTH: 31
<212> TYPE: DNA
<213> ORGANISM: Artificial
<220> FEATURE:
<223> OTHER INFORMATION: synthesized

<400> SEQUENCE: 2
gtcgactcat ccattataac aacacattca c                                      31

<210> SEQ ID NO 3
<211> LENGTH: 46
<212> TYPE: DNA
<213> ORGANISM: Artificial
<220> FEATURE:
<223> OTHER INFORMATION: synthesized

<400> SEQUENCE: 3
cacacaggaa acagaccatg caccatcacc atcaccatcg ttacgg                      46

<210> SEQ ID NO 4
<211> LENGTH: 46
<212> TYPE: DNA
<213> ORGANISM: Artificial
<220> FEATURE:
<223> OTHER INFORMATION: synthesized

<400> SEQUENCE: 4
ccgtaacgat ggtgatggtg atggtgcatg gtctgtttcc tgtgtg                      46

<210> SEQ ID NO 5
<211> LENGTH: 2932
<212> TYPE: DNA
<213> ORGANISM: Clostridium stercorarium

<400> SEQUENCE: 5
```

-continued

| | | | | | |
|---|---|---|---|---|---|
| atgcgttacg | gttattttga | tgaaaaagcc | cgcgaatatg | ttattacaag | acccgatact | 60 |
| ccgacaccat | ggataaacta | cataggcaac | gggaaatacg | gaggcatagt | tacaaacacc | 120 |
| ggaggcggct | acagttttca | caaggaccca | cagaacagaa | gaattacaag | atacagatac | 180 |
| aacaatctcc | ccaccgacag | gccgggcagg | tatatttacg | tccgcgacag | gctgacgggc | 240 |
| gaatactgga | atcccggcta | tcagcccgtg | cagagaaaac | tcgactctta | caggtgcagg | 300 |
| catggaatgg | gttatactgt | tctcgaaggg | gagtacaagg | gcattgcagc | cgatgtgacc | 360 |
| tattttgtac | ccgatgacag | ggactttgaa | atctggcttg | tacaaatcag | aaacctctgc | 420 |
| catgttgaaa | gaaaccttca | ggtcttcagt | tacgccgaat | tctgtttctg | ggatgccata | 480 |
| atggatcagc | agaatgtgga | ctgggttcag | cagataaacc | agggaaggta | tgaagacagg | 540 |
| cttataacgt | ggcatccgca | tcattttaag | gacgcatgcg | cattctttgc | cacaaatgcc | 600 |
| gaaataaaca | gttttgatac | caatcttgag | gcgtttatcg | gaagataccg | ctgcgaatct | 660 |
| aaccccatcg | ccgtggaaac | agggcatgt | tccaattccg | tgtcttacag | aatgaacggt | 720 |
| gtcggtgcgt | tttgcatcga | cgtaaattta | aaaccggggg | aagagcggga | aattatattt | 780 |
| attttgggct | ttaccgaaaa | caagagtaca | ataagggacg | aaatccgcga | ttaccttaac | 840 |
| gtggaatatg | caaagaagc | tctaaaaagg | ctaaggact | cctgggagga | atatctggac | 900 |
| aaactgcaga | ttgaaacccc | cgatcgggaa | accaatctct | tgttaacac | atggaatcag | 960 |
| tatcagtgca | aaataacctt | caactggtca | agatttgtat | cgatgtacag | ctggggctg | 1020 |
| ggaaggggaa | tagggatcag | ggacagcgcc | caggacacgc | tcggcgttat | gcattcaata | 1080 |
| cccgagctgg | caggcgggct | tattaaacgg | ttaattcact | gccagtatac | cgacgggcgt | 1140 |
| gtttatcatc | tgttttttccc | tttgacaggc | gaaggcggga | tcggtgacgc | cccagttgtg | 1200 |
| aaatttgact | ggtattccga | tgatcatctg | tggctgccca | tcgccgcaaa | cgcatatctg | 1260 |
| aaggaaacgg | cgaatttcga | ttttttccaa | agtgttgtgc | cgtataacga | caataaaacc | 1320 |
| gaaggtaccg | tatgggagca | tctcaacagg | gccatggaat | tcacatacaa | ccaccgcgga | 1380 |
| ccgcacgcct | tgccttatag | cagagccgac | tggaacgata | ccctgaacct | ggatatggga | 1440 |
| aacggaatag | ccgaaactct | ttttacttca | atgcttttct | cagagccgcc | cttgaaacga | 1500 |
| ttcagatgcc | gaatatccga | caaaaggatt | gcgacaaaat | accggtattg | gtatgatgaa | 1560 |
| atgaaacaag | cctaaatga | atggtgctgg | gacggagaat | ggtacataag | gcatttgac | 1620 |
| gatgagggta | atgtccttgg | ttcgggtaaa | aacagatacg | ggaaaatttt | cattaacagc | 1680 |
| cagtcatggg | cggttcttag | catggttgcg | cccgaagaat | acgctaagaa | atgcctcgag | 1740 |
| tcggtttatc | ggcacctgaa | cacgaagtac | gggatagtta | agtatatcc | ggcatatccg | 1800 |
| gaatataatc | cgaaaatagg | gggcatgacc | acatacccgc | cggggcgaa | ggaaaacggc | 1860 |
| ggtatttttg | cccataccaa | cccatgggta | atgattgccg | aatgtatgat | gggcaacgga | 1920 |
| aggcgggctt | atcagtacta | caggcagata | ctcccgttaa | cgcgcaatga | cgacgccgat | 1980 |
| ttgcttgaag | tggaacctta | cgtgtactgc | cagaatatac | tcgaaaagga | gcatccgcag | 2040 |
| ttcggaatag | gccgtaattc | gtggcttaca | ggcactgcag | catggaatat | ggttgcggta | 2100 |
| agccagtata | ttttgggaat | aagaccggaa | tacgacggcc | tgacggtgga | tccgtgcatt | 2160 |
| ccgcctgact | ggaaaggttt | taaagtgaga | agaattttcc | ggggttgtgt | ttacaatatc | 2220 |
| gaagtaagaa | atcctgaagg | cgtacggagg | tgtgaaaaaa | attgtcgtag | aggagttgaa | 2280 |
| accgacaaaa | tacccgtaaa | acctgcagga | acggttgtg | aatgtgttgt | tataatggga | 2340 |
| tgactgtaaa | aaagtaaaaa | tatttaaaca | tataagttca | tcagcgggaa | cttttttacca | 2400 |

-continued

```
gtatatgcgt ctaatcaaac gtaactggca acccgctgca aaacaaatta aaaaagcata   2460
gttcacaact tcaggttgcg gctatgcttt ttttcactga aaatttcact gaaaaactta   2520
taccgtcatt acgggaataa ggaggggtta tatgaagaaa aatgctttac ttgttttaat   2580
gttcattttg ataattttt ccggttgtac gggtggcgga aacgtcaccg atacaacgct   2640
gaaacccgag tcagggaaa cggcaggcac taccgttgat gaaagagcc agccctcagc    2700 cagagttttcc gacgcaaata aaatttttc ctgggaactg ttcaaagcgc ttaacgcgga   2760
ggaatcaaaa caggaaactt ttatctctcc gttttcggtt tcggcagtgc ttatgatggc   2820
ctataacggc gcagagggaa gcacgcggga agcaatggcc aaagcgatgc attatggtgg   2880
catgtccgtt gatgaattaa acagtgaata caggaatttg ttaaacagac tg           2932
```

<210> SEQ ID NO 6
<211> LENGTH: 780
<212> TYPE: PRT
<213> ORGANISM: Clostridium stercorarium

<400> SEQUENCE: 6

```
Met Arg Tyr Gly Tyr Phe Asp Glu Lys Ala Arg Glu Tyr Val Ile Thr
1               5                   10                  15

Arg Pro Asp Thr Pro Thr Pro Trp Ile Asn Tyr Ile Gly Asn Gly Lys
                20                  25                  30

Tyr Gly Gly Ile Val Thr Asn Thr Gly Gly Gly Tyr Ser Phe His Lys
            35                  40                  45

Asp Pro Gln Asn Arg Arg Ile Thr Arg Tyr Arg Tyr Asn Asn Leu Pro
        50                  55                  60

Thr Asp Arg Pro Gly Arg Tyr Ile Tyr Val Arg Asp Arg Leu Thr Gly
65                  70                  75                  80

Glu Tyr Trp Asn Pro Gly Tyr Gln Pro Val Gln Arg Lys Leu Asp Ser
                85                  90                  95

Tyr Arg Cys Arg His Gly Met Gly Tyr Thr Val Leu Glu Gly Glu Tyr
                100                 105                 110

Lys Gly Ile Ala Ala Asp Val Thr Tyr Phe Val Pro Asp Asp Arg Asp
            115                 120                 125

Phe Glu Ile Trp Leu Val Gln Ile Arg Asn Leu Cys His Val Glu Arg
        130                 135                 140

Asn Leu Gln Val Phe Ser Tyr Ala Glu Phe Cys Phe Trp Asp Ala Ile
145                 150                 155                 160

Met Asp Gln Gln Asn Val Asp Trp Val Gln Gln Ile Asn Gln Gly Arg
                165                 170                 175

Tyr Glu Asp Arg Leu Ile Thr Trp His Pro His His Phe Lys Asp Ala
            180                 185                 190

Cys Ala Phe Phe Ala Thr Asn Ala Glu Ile Asn Ser Phe Asp Thr Asn
        195                 200                 205

Leu Glu Ala Phe Ile Gly Arg Tyr Arg Cys Glu Ser Asn Pro Ile Ala
    210                 215                 220

Val Glu Thr Gly Ala Cys Ser Asn Ser Val Ser Tyr Arg Met Asn Gly
225                 230                 235                 240

Val Gly Ala Phe Cys Ile Asp Val Asn Leu Lys Pro Gly Glu Glu Arg
                245                 250                 255

Glu Ile Ile Phe Ile Leu Gly Phe Thr Glu Asn Lys Ser Thr Ile Arg
            260                 265                 270

Asp Glu Ile Arg Asp Tyr Leu Asn Val Glu Tyr Ala Lys Glu Ala Leu
```

```
                275                 280                 285
Lys Arg Leu Lys Asp Ser Trp Glu Glu Tyr Leu Asp Lys Leu Gln Ile
            290                 295                 300
Glu Thr Pro Asp Arg Glu Thr Asn Leu Phe Val Asn Thr Trp Asn Gln
305                 310                 315                 320
Tyr Gln Cys Lys Ile Thr Phe Asn Trp Ser Arg Phe Val Ser Met Tyr
                325                 330                 335
Ser Trp Gly Leu Gly Arg Gly Ile Gly Ile Arg Asp Ser Ala Gln Asp
            340                 345                 350
Thr Leu Gly Val Met His Ser Ile Pro Glu Leu Ala Gly Gly Leu Ile
            355                 360                 365
Lys Arg Leu Ile His Cys Gln Tyr Thr Asp Gly Arg Val Tyr His Leu
            370                 375                 380
Phe Phe Pro Leu Thr Gly Glu Gly Ile Gly Asp Ala Pro Val Val
385                 390                 395                 400
Lys Phe Asp Trp Tyr Ser Asp Asp His Leu Trp Leu Pro Ile Ala Ala
                405                 410                 415
Asn Ala Tyr Leu Lys Glu Thr Ala Asn Phe Asp Phe Gln Ser Val
            420                 425                 430
Val Pro Tyr Asn Asp Asn Lys Thr Glu Gly Thr Val Trp Glu His Leu
            435                 440                 445
Asn Arg Ala Met Glu Phe Thr Tyr Asn His Arg Gly Pro His Ala Leu
450                 455                 460
Pro Tyr Ser Arg Ala Asp Trp Asn Asp Thr Leu Asn Leu Asp Met Gly
465                 470                 475                 480
Asn Gly Ile Ala Glu Thr Leu Phe Thr Ser Met Leu Phe Ser Glu Pro
                485                 490                 495
Pro Leu Lys Arg Phe Arg Cys Arg Ile Ser Asp Lys Arg Ile Ala Thr
            500                 505                 510
Lys Tyr Arg Tyr Trp Tyr Asp Glu Met Lys Gln Ala Ile Asn Glu Trp
            515                 520                 525
Cys Trp Asp Gly Glu Trp Tyr Ile Arg Ala Phe Asp Asp Glu Gly Asn
            530                 535                 540
Val Leu Gly Ser Gly Lys Asn Arg Tyr Gly Lys Ile Phe Ile Asn Ser
545                 550                 555                 560
Gln Ser Trp Ala Val Leu Ser Met Val Ala Pro Glu Glu Tyr Ala Lys
                565                 570                 575
Lys Cys Leu Glu Ser Val Tyr Arg His Leu Asn Thr Lys Tyr Gly Ile
            580                 585                 590
Val Lys Val Tyr Pro Ala Tyr Pro Glu Tyr Asn Pro Lys Ile Gly Gly
            595                 600                 605
Met Thr Thr Tyr Pro Pro Gly Ala Lys Glu Asn Gly Gly Ile Phe Ala
610                 615                 620
His Thr Asn Pro Trp Val Met Ile Ala Glu Cys Met Met Gly Asn Gly
625                 630                 635                 640
Arg Arg Ala Tyr Gln Tyr Tyr Arg Gln Ile Leu Pro Leu Thr Arg Asn
                645                 650                 655
Asp Asp Ala Asp Leu Leu Glu Val Glu Pro Tyr Val Tyr Cys Gln Asn
            660                 665                 670
Ile Leu Gly Lys Glu His Pro Gln Phe Gly Ile Gly Arg Asn Ser Trp
            675                 680                 685
Leu Thr Gly Thr Ala Ala Trp Asn Met Val Ala Val Ser Gln Tyr Ile
            690                 695                 700
```

-continued

```
Leu Gly Ile Arg Pro Glu Tyr Asp Gly Leu Thr Val Asp Pro Cys Ile
705                 710                 715                 720

Pro Pro Asp Trp Lys Gly Phe Lys Val Arg Arg Ile Phe Arg Gly Cys
            725                 730                 735

Val Tyr Asn Ile Glu Val Arg Asn Pro Glu Gly Val Arg Arg Cys Glu
            740                 745                 750

Lys Asn Cys Arg Arg Gly Val Glu Thr Asp Lys Ile Pro Val Lys Pro
        755                 760                 765

Ala Gly Thr Val Cys Glu Cys Val Val Ile Met Gly
        770             775                 780
```